United States Patent [19]

Jordan

[11] Patent Number: 4,880,637

[45] Date of Patent: * Nov. 14, 1989

[54] COMPOSITIONS OF CATECHOLIC BUTANES WITH ZINC

[75] Inventor: Russell T. Jordan, Fort Collins, Colo.

[73] Assignee: Chemex Pharmaceuticals, Inc., Denver, Colo.

[*] Notice: The portion of the term of this patent subsequent to Sep. 27, 2005 has been disclaimed.

[21] Appl. No.: 924,620

[22] Filed: Oct. 28, 1986

Related U.S. Application Data

[63] Continuation-in-part of Ser. No. 699,923, Feb. 11, 1985, abandoned, which is a continuation-in-part of Ser. No. 578,501, Apr. 9, 1984, abandoned, which is a continuation-in-part of Ser. No. 465,631, Feb. 10, 1983, abandoned, which is a continuation-in-part of Ser. No. 365,781, Apr. 5, 1982, abandoned, which is a continuation-in-part of Ser. No. 49,886, Jun. 19, 1979, abandoned.

[51] Int. Cl.$^4$ .................. A61K 33/30; A61K 31/08; A61K 31/02

[52] U.S. Cl. ................... 424/641; 514/731; 514/736; 514/859; 514/863

[58] Field of Search ............... 424/131, 145; 514/731, 514/736, 863, 859

[56] References Cited

U.S. PATENT DOCUMENTS 4,774,229 9/1988 Jordan .................... 514/25

OTHER PUBLICATIONS

Dyer, An Index of Tumor Chemotherapy, PHS, pp. 10, 12, 40, 79, 80, 81, 1949.

Primary Examiner—John W. Rollins
Attorney, Agent, or Firm—Kenyon & Kenyon

[57] ABSTRACT

The present invention provides new compositions comprising catecholic butanes and ionic zinc. The invention also relates to pharmacologically active compositions comprising said new compositions, which are useful in the treatment of benign, premalignant and malignant solid tumors, especially those of the skin. The ionic zinc may be in the form of a zinc salt, and the preferred catecholic butane is nordihydroguaiaretic acid.

25 Claims, No Drawings

COMPOSITIONS OF CATECHOLIC BUTANES WITH ZINC

CROSS REFERENCE TO RELATED APPLICATIONS

This application is a continuation-in-part of copending application Ser. No. 699,923 filed Feb. 11, 1985, now abandoned, which is a continuation-in-part of application Ser. No. 578,501 filed Apr. 9, 1984, now abandoned, which is a continuation-in-part of application Ser. No. 465,631, filed Feb. 10, 1983, now abandoned, which is a continuation-in-part of application Ser. No. 365,781 filed Apr. 5, 1982, now abandoned, which is a continuation-in-part of application Ser. No. 49,886 filed June 19, 1979, now abandoned.

FIELD OF THE INVENTION

This invention relates to new compositions comprising the herein defined catecholic butanes and ionic zinc, which ionic zinc may be derived from water-soluble zinc salts present in the composition. The invention also relates to pharmacologically active compositions comprising said new compositions; the use thereof for the treatment of benign, premalignant and malignant solid tumors, especially those of the skin. They are also useful in the treatment of diseases and disorders of the skin such as acne and psoriasis, in aiding the healing of skin wounds and breaks in the skin and for antiviral, antibacterial and antifungal uses.

BACKGROUND

Methods of treating premalignant and malignant growths of the skin have often been traumatic. A common method of treating disorders such as actinic keratosis has been the application of liquid nitrogen to destroy the affected tissue. Epidermal tumors are commonly treated by physical removal through surgery. A method which has been used in the past is chemosurgery through the application of escharotic or fixative chemicals such as zinc chloride. This has not been found to be particularly effective because of the physical discomfort associated with the use of such materials. It also has the disadvantage of destroying both healthy tissue and the diseased tissue.

The use of known antitumor drugs has not been found to be particularly effective in the treatment of skin tumors since these drugs are commonly applied systemically resulting in substantial side effects due to their toxicity. The naturally occurring meso form of the catecholic butane, nordihydroguaiaretic acid [meso-1,4-bis (3,4-dihydroxyphenyl)-2,3-dimethylbutane] ("NDGA") was reported as providing a positive result against malignant melanoma, C. R. Smart, et al., *Rocky Mountain Medical Journal*, Nov. 1970, pp. 39–43 (unless otherwise indicated, NDGA is used herein to refer to the meso form of nordihydroguaiaretic acid). NDGA is found in the creosote bush, and this plant was used for centuries to brew a tea which was the basis for a folk remedy that called for drinking the tea to cure colds, rheumatism and other ailments. However, this remedy has not proven to be successful.

A clinical study was conducted by Smart, et al. in which human cancer patients ingested either a tea made from the creosote bush or doses of pure NDGA. This study indicated that neither NDGA nor the tea were effective anticancer agents and in some cases caused stimulation of tumor cell growth. This confirmed the earlier screening studies of NDGA conducted by Leiter et al. of the Cancer Chemotherapy National Service Center of the National Cancer Institute which obtained negative results when NDGA was tested against several types of cancer cells.

The general structure for nordihydroguaiaretic acid (generic to all of its stereoisomeric forms) is given in Formula (I).

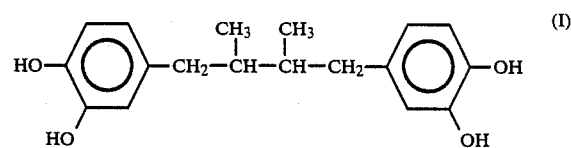

Surprisingly, it has been discovered that the catecholic butane, nordihydroguaiaretic acid, and/or derivatives thereof as defined herein, in a pharmaceutical composition that includes ionic zinc, is effective in treating benign, premalignant and malignant growths of the skin without the detrimental side effects associated with chemotherapy or chemosurgical techniques. The compositions provide their advantageous results when applied topically to the afflicted area of the skin, or injected into the growth. As disclosed in copending application Ser. No. 699,923, such compositions are also effective in treating disorders of the skin including acne and psoriasis, in aiding in the healing of skin wounds and in alleviating bacterial, viral and fungal infections when applied to the situs of the disorder. The compositions are also useful in the treatment for warts.

SUMMARY OF THE INVENTION

In a compositional aspect, this invention relates to compositions comprising a catecholic butane of formula:

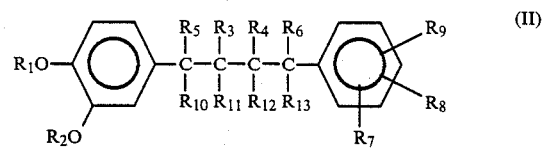

wherein $R_1$ and $R_2$ are independently H, lower alkyl or lower acyl;

$R_3$, $R_4$, $R_5$ and $R_6$ are independently H or lower alkyl;

$R_7$, $R_8$ and $R_9$ are independently H, hydroxy, lower alkoxy or lower acyloxy;

$R_{10}$, $R_{11}$, $R_{12}$ and $R_{13}$ are independently H or lower alkyl; and ionic zinc.

Lower alkyl is intended to generally mean $C_1$–$C_6$ alkyl, and preferably $R_3$ and $R_4$ are $C_1$–$C_3$ alkyl. Lower acyl is intended to generally mean [$C_1$–$C_6$] acyl, with [$C_2$–$C_6$] acyl being preferred. It will be appreciated by those skilled in this art that Formula II is directed to both the phenolic compounds and the conventional esters and ethers thereof.

In a compositional aspect, the invention relates to pharmaceutical compositions adapted for topical, parenteral, subcutaneous, or intralesional administration comprising, in admixture with a pharmaceutically acceptable carrier, (a) a mixture of (i) a catecholic butane of Formula (II), and (ii) a pharmaceutically acceptable source of ionic zinc. Preferred compositions of this invention are adapted for topical application to a situs or for injection into the interior or near vicinity of the afflicted situs. The preferred compositions comprise nordihydroguaiaretic acid and, preferably, a source of ionic zinc, and such compositions in combination with pharmaceutically acceptable carriers.

The pharmaceutical aspects of this invention include methods for inhibiting the abnormal growth or proliferation of cells in mammals which comprise applying directly to the situs of abnormal growth of cells an amount of said catecholic butane and ionic zinc effective to inhibit said growth.

In a further method of use aspect, this invention defines methods of increasing the oxidative stability of catecholic butanes of Formula (II), which comprise mixing with said catecholic butanes an oxidation inhibiting amount of a source of ionic zinc.

In a still further method of use aspect, this invention relates to methods of increasing the retention time of applied catecholic butanes at the situs of dermal afflictions. This is accomplished by applying a composition according to this invention comprising said catecholic butane and an amount of a source of ionic zinc that is effective to increase said retention time.

DETAILED DESCRIPTION OF THE INVENTION

The term "source of ionic zinc" as used herein means a compound comprising ionic zinc in salt or chelated form, as opposed to, in a practical sense, metallic zinc and zinc compounds that do not ionize in the environment of the compositions of this invention. That source can be or can include a salt or chelate of the catecholic butane itself. When used herein, "zinc" means zinc in its ionic or divalent state as noted, and not metallic zinc.

The term "afflicted situs or area" or similar language, as used herein, refers to a localized area of pathology, infection, wound, lesion, or abnormal cells, including tumors, and the surrounding area.

The term "applying" as used herein embraces both topical applications to a surface of the afflicted situs and injection into the interior of the situs.

The term "mammal" as used herein includes feline, canine, equine, bovine, rodent and primate species, including cats, dogs, horses, rats, mice, monkeys and humans. Other animals e.g., birds, can also be successfully treated with the compositions of this invention.

The term "abnormal growth of cells" refers to benign, premalignant and malignant cells. Examples of the former include the cells associated with adenomas, papillomas, etc. Examples of premalignant cells include actinic keratosis.

The term "escharotic" means a corrosive or caustic agent which is capable of killing healthy, living cells.

The term "nonescharotic concentration" means a concentration of the source of ionic zinc which does not kill living cells upon contact, e.g., as does zinc chloride when employed as an escharotic agent at concentrations of about 40 weight percent or higher, depending on the delivery vehicle.

The term "solid tumor" refers to tumors in which a plurality of tumor cells are associated with one another, i.e. contiguous and localized within a confined site. This is to be contrasted with "fluid" or "hematogenous" tumors in which the tumor cells occur primarily as unassociated or individual cells, e.g. leukemia. Solid tumors generally propagate on host tissues such as the epithelial, the connective and supportive tissues as well as other tissues located throughout the body. Examples of epithelial tumors include papillomas such as Verruca Verruciformis and carcinomas such as squamous cell carcinoma, basal cell carcinoma, adenoma, adenocarcinoma, cystadenoma, cystadenocarcinoma and Bowenoid carcinoma. Examples of supportive and connective tissue tumors include sarcomas and their benign counterparts such as fibrosarcoma, fibroma, liposarcoma, lipoma chondrosarcoma, chondroma, leiomysarcoma, and leimyoma. Examples of other tissue tumors include gliomas (brain tumors) and malignant melanomas.

The term "pharmaceutically-acceptable carrier" refers to a material that is non-toxic, generally inert and does not adversely affect the functionality of the active ingredients.

Compositions according to the invention comprising catecholic butanes and zinc are particularly effective for the treatment of a variety of solid tumors and skin disorders. Improved results are obtained when the afflicted areas are directly contacted with the instant compositions. The instant compositions have been found to unexpectedly provide improved restoration of integrity to injured tissue and cause the regression or elimination of solid tumors. In addition, the presence of zinc has also been found to substantially increase the stability of the catecholic butanes to oxidative reactions. The catecholic butanes and zinc show no evidence of pharmacological antagonism.

The compositions of the instant invention have been found to be particularly effective against the following solid mammalian tumors: mouse Sarcoma-180; human tumors including malignant melanoma, Sarcoma-180, squamous cell carcinoma, lung squamous cell carcinoma, breast adenocarcinoma, glioma, glioastrocytoma, renal-cell carcinoma, colon, Bowenoid carcinoma and basal cell carcinoma; equine tumors including papillomas, malignant melanoma, sarcoid and squamous cell carcinoma; and canine tumors including squamous cell carcinoma, breast adenocarcinoma, perianal adenoma, basal cell carcinoma and mast cell tumor.

With such compositions it has also been found that, surprisingly, the catecholic butanes are retained by the tissue at the treatment site for a significantly longer period of time than in the absence of these compositions. This unexpected property of the instant compositions improves the effectiveness of the treatment and also acts to minimize any detrimental side effects of the compositions. Additionally, the combination of catecholic butane and ionic zinc allows the concentration of each component to be reduced while maintaining the efficacy of the composition thus increasing the safety of the compositions.

The novel compositions of this invention are particularly useful as antitumor agents and in the treatment of keratoses, especially actinic keratosis and including senile keratotic lesions. They are useful in ameliorating a wide variety of premalignant and malignant skin tumors, basal cell carcinoma, squamous cell carcinoma and a diversified variety of melanotic lesions which are premalignant or malignant as well as certain cutaneous tumor manifestations of otherwise systemic diseases. The compositions have been found to be effective against solid tumors arising from all three embryonic tissue types, namely squamous cell carcinoma, e.g., lung carcinoma, arising from the ectodermal layer; adenocarcinomas, e.g. breast, renal and colon cancer, arising from the endodermal layer; and melanoma and brain cancers, arising from the mesodermal layer.

The catecholic butanes useful in the compositions of the instant invention are of the Formula (II), and are commonly available from Aldrich Chemical Co., Milwaukee, Wis. or can be synthesized by known methods. Illustrative classes of compounds within the scope of Formula (II) are those wherein:

(a) one or more of $R_1$, $R_2$, $R_3$, $R_4$, $R_5$, $R_6$, $R_7$, $R_8$, $R_9$, $R_{10}$, $R_{11}$, $R_{12}$ and $R_{13}$ are H, e.g., those wherein $R_5$ is H, $R_5$ and $R_6$ are H or $R_5$, $R_6$ and $R_7$ are H and $R_8$ and $R_9$ are OH or $OR_1$;

(b) $R_3$ and $R_4$ each are $CH_3$ or $C_2H_5$ including those of (a), especially those wherein $R_5$, $R_6$ and $R_7$ are H and/or $R_8$ and $R_9$ are OH and $OR_1$;

(c) $R_1$ and $R_2$ are lower acyl, e.g., hydrocarbonacyl, preferably, alkanoyl, e.g., acetyl, propionyl, etc., including those of (a) and (b);

(d) $R_1$ and $R_2$ are alike and $R_8$ and $R_9$ are $OR_1$, including those of (a), (b) and (c); and (e) The compound is in the form of a single optical isomer or a mixture of such isomers, e.g., a racemic mixture, or diastereoisomers including each of (a), (b), (c) and (d).

As used herein, lower alkyl represents, inter alia, methyl, ethyl, n-propyl, isopropyl, n-butyl, iso-butyl, tert-butyl, n-pentyl, isopentyl, n-hexyl, and the like.

Lower acyl represents groups having the general formula RCO—, e.g., acetyl ($CH_3CO$—), propionyl ($CH_3CH_2CO$—), butyryl ($CH_3CH_2CH_2CO$—), and the like. When the catecholic butane compound is named as a substituted phenyl, the corresponding groups are acetoxy ($CH_3CO_2$—), propionyloxy ($CH_3CH_2CO_2$—), and butyroyloxy ($CH_3CH_2CH_2CO_2$—).

Examples of catecholic butanes include the d-, l-, racemic mixture of d- and l-, and meso-isomers of 1,4-bis(3,4-dihydroxyphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethyl-butane; 1,4-bis(3,4-dipropoxyphenyl)-2,3-dimethylbutane; 1-(3,4-dihydroxyphenyl)-4-(3',4',5'-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis( 3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; 1-(3,4-dihydroxyphenyl)-4-phenylbutane and 1-(3,4-dihydroxyphenyl-4-(2,5 dihydroxyphenyl) butane. Mixtures of the Formula (II) catecholic butanes may be used in the instant compositions.

The zinc is present in the instant compositions as a cation, e.g., as a salt or a chelate of the catecholic butane itself or as a cation of a pharmaceutically acceptable water-soluble salt, or as a mixture thereof. Pharmaceutically acceptable salts include those of inorganic acids such as nitrate, sulfate, halides, phosphates, those of organic acids, such as acetate, benzoate, carbonate, citrate, caprylate, gluconate, and others well known to those skilled in this art, and mixtures thereof. Zinc chloride is especially preferred. As stated above, the term "zinc", as used herein, means ionic zinc, rather than zinc metal.

While ionic zinc is preferred for use in the compositions according to the invention, it has been observed that other metals in the ionic state, e.g., copper, vanadium and iron, have been found to be useful in the instant compositions.

The molar ratio of catecholic butane to zinc in the compositions of this invention may be varied over a wide range. The range of the molar ratio may be as broad as between 100:1 and 1:100. However, at the extremes of this range the advantageous effects of the new composition are minimal. More commonly the range is between about 10:1 and 1:20. Preferably, the molar ratio ranges between about 5:1 and 1:15, and most preferably, ranges between about 3:1 and 1:10.

The proper ratios are those which result in the composition exhibiting the property or properties required in the treatment for which the composition is being used, namely, one or more of anti-tumor activity and antioxidant activity. The preferred molar ratio range depends upon the particular condition being treated as well as the method of delivery of the composition to the treatment site and for any specific application which may be determined by normal pharmacological screening methods used in the art such as against the particular strain of tumor cells. If desired, an excess of the zinc or the catecholic butane can be used as appropriate for the specific condition being treated.

Generally, preferred molar ratios of the catecholic butanes to zinc with respect to two classes of tumors and exemplary application amounts/rate are shown in Table I.

TABLE I

| Treatment/Use | Preferred Ratio of Catecholic Butane/Zinc | Exemplary Application Amount/Rate of Catechol/Zinc Comcosition |
|---|---|---|
| Pre-Malignant Tumors | 1:5–5:1<br>1–10% cat. but./<br>15–1% zinc | Apply topically 2–150 mg/cm$^2$ of tumor. Repeat application when amount of prior application falls below about 5 mg/cm$^2$. Wound may be dressed until healing is complete. Healing period may extend for several months. Repeat daily |
| Solid Epithelial Tumors | 1:15–5:1<br>1–10% cat. but./<br>30–1% zinc | as indicated by observation of tumor size reduction (i.e., if no reduction in size after 10 days, repeat 2–3 times daily; if reduction in size is served, after 10 days, repeat at daily intervals or sooner if reduction in size ceases to continue. Healing period may extend for several months. Alternatively, 0.1–20 ml. of composition may be injected intralesion- |

TABLE I-continued

| Treatment/Use | Preferred Ratio of Catecholic Butane/Zinc | Exemplary Application Amount/Rate of Catechol/Zinc Comcosition |
| --- | --- | --- |
| | | ally at the tumor site. |

The instant compositions can be applied topically to or injected into the treatment site, e.g., solid tumor, subcutaneously by injection, for example. When used for topical applications, the catecholic butane and the source of ionic zinc are usually formulated with a pharmaceutically-acceptable carrier. Carrier materials are well known in the pharmaceutical formulation art and include those materials referred to as diluents or vehicles. The carrier may include inorganic or organic materials and should have sufficient viscosity to allow spreading of the composition and provide good adherence to the tissue to which it is topically applied. Examples of such carriers include, without limitation, polyols such as glycerol, propylene glycol, polyethylene glycol, preferably of a molecular weight between about 400 and about 8000, suitable mixtures thereof, vegetable oils, and other materials well known to those skilled in this art. The viscosity of the formulation can be adjusted by methods well known in the art, for example, by the use of a higher molecular weight polyethylene glycol.

In addition to the catecholic butane, source of ionic zinc and carrier, the formulation can contain pharmacologically-acceptable additives or adjuvants such as antimicrobial agents, e.g. methyl, ethyl, propyl, and butyl esters of para-hydroxybenzoic acid as well as chlorobutanol, phenol, ascorbic acid, etc. The formulation can also contain thickening or gelling agents, emulsifiers, wetting agents, coloring agents, buffers, stabilizers and preservatives including antioxidants such as butylhydroxyanisole in accordance with the practice of the art. The formulation can also contain penetration enhancers such as dimethyl sulfoxide, long-chain alcohols such as nonoxynol, long-chain carboxylic acids, propylene glycol, N-(2-hydroxyethyl)pyrrolidone,1-dodecyl-azacycloheptan-2-one, and the like. Depending on the method of application and the disease being treated, it may be desirable to use absorption-delaying agents such as aluminum monostearate and gelatin.

The composition of the formulation can be adjusted using components well-known in the formulation art to provide a pharmaceutical formulation which is a gel, cream, ointment, solid, liquid, semi-solid, etc. The particular physical form of the formulation depends on the desired method of treatment and the patient to be treated.

Typical formulations of the pharmaceutical compositions of this invention are set forth in Table II.

TABLE II

| Application Form | Formulation | (Per 100 mgs.) | |
| --- | --- | --- | --- |
| Ointment | Zinc chloride | 10.0 | (preferred range: about 0.05-35) |
| | Catecholic butane | 5.0 | (preferred range: about 0.1-30) |
| | Peg 400 | 4.2 | |
| | Peg 8000 | 61.7 | |
| | Water | 19.0 | |
| | Ascorbic acid | 0.1 | |
| Gel | Zinc chloride | 10.0 | (preferred range: about 0.05-35) |
| | Catecholic butane | 5.0 | (preferred range: about 0.1-30) |
| | Standard denatured alcohol | 10.0 | |
| | Propylene glycol | 22.5 | |
| | Water | 43.4 | |
| | Non-ionic surfactant | 6.0 | |
| | Xantham gum | 3.0 | |
| | Ascorbic acid | 0.1 | |
| Cream | Zinc chloride | 10.0 | (preferred range: about 0.05-35) |
| | Catecholic butane | 5.0 | (preferred range: about 0.1-30) |
| | Ascorbic acid | 0.1 | |
| | Benzyl alcohol | 5.0 | |
| | Propylene glycol | 23.0 | |
| | Water | 25.4 | |
| | Stearyl alcohol | 7.0 | |
| | Cetyl alcohol | 4.5 | |
| | White petrolatum | 13.0 | |
| | Poloxyl-40 stearate | 7.00 | |
| Solid | Zinc chloride | 5.00 | (preferred range: 0.05-35) |
| | Catecholic butane | 5.00 | (preferred range: 0.1-30) |
| | Carnuba wax | 8.88 | |
| | Beeswax | 13.32 | |
| | Lanolin anhydrous | 4.44 | |
| | Cetyl alcohol | 4.44 | |
| | Ascorbic acid | 0.10 | |
| | Castor oil | 57.70 | |
| | Water | 1.20 | |
| Injectible Liquid | Zinc sulfate.7H$_2$O | 2.00 | (preferred range: 0.05-35) |
| | Catecholic butane | 1.05 | (preferred range: 0.1-30) |
| | Water | 33.94 | |
| | Glycerine | 36.44 | |
| | Glycine | 1.52 | |
| | Sodium ascorbate | 0.05 | |
| | Propylene glycol | 25.00 | |

For administration by injection, the compositions according to the invention are formulated as solutions or suspensions having a low enough viscosity to be injected. The composition suitable for injectable use must be sterile and fluid to the extent that easy syringe injection exists. It should also be stable under conditions of manufacture and storage and be preserved against contamination by microorganisms. Preservatives include alcohol, benzoic acid, sorbic acid, and methyl and propyl paraben with and without propylene glycol. Additionally, the pH of the composition must be within a range which does not result in tissue damage, namely, between about 3-7.5.

The concentration of the catecholic butane and the ionic zinc in a particular formulation depends on the condition being treated, the method of application, i.e. topical or injection, the rate of delivery of the active ingredient(s) to the treatment site, and the number of applications of the formulation which can be used. Additionally, certain catecholic butane compounds are more effective in treating particular conditions than are other analogs. The concentration of ionic zinc in the formulation likewise depends upon the condition being treated and the particular catecholic butane or combination of butanes being used. As discussed hereinabove, it may be desirable to have a substantial excess of one component, for example, ionic zinc, present in the formulation in order to effectively treat the particular condition.

In practice, it is preferred that a formulation contain the lowest concentrations of catecholic butane and ionic zinc which effectively treat the condition with the desired number of applications, i.e., a lower effective dose rate can be tolerated if multiple applications are used. This low concentration limit is dependent upon the delivery effectiveness of the carrier vehicle. Preferably, the catecholic butane and zinc together comprise between about 0.5 and about 80 weight percent of the formulation. It may be possible to use lower concentrations depending on its delivery to the tumor by the carrier. In the treatment of solid tumors, the formulation preferably contains between about 0.1 and about 30 weight percent catecholic butane and between about 0.05 and about 35 weight percent zinc. Preferably at least one of the catecholic butane and the zinc is present in the formulation at a concentration of at least about 0.5 weight percent, and more preferably, at least about 1.0 weight percent. As used herein, the weight percent in the formulations refers to the concentrations of materials being effectively delivered to the treatment site.

As stated above, formulations may be prepared that have significantly higher concentrations of catecholic butanes and zinc depending upon the carrier and additives being used. If the carrier substantially retains the catecholic butane and zinc or releases them at a slow rate, the concentrations of these materials in the formulation should be substantially increased to provide an effective treatment. The concentrations of active ingredients in a particular formulation required to provide a particular effective dose may be generally determined by a person skilled in the pharmaceutical formulation art based upon the properties of a carrier and the particular additives introduced into the formulation. A formulation which is being applied topically may contain a higher concentration of catecholic butane and zinc than a composition being injected, for example, into a solid tumor.

A preferred embodiment of the instant invention comprises compositions containing nordihydroguaiaretic acid, i.e., meso 1,4-bis(3,4-dihydroxyphenyl)-2,3-dimethylbutane, and zinc chloride. This combination has been found to be particularly effective in treating actinic keratosis and solid tumors. Since zinc chloride at high concentrations is an escharotic material, it is preferred that the concentration of zinc chloride delivered to the treatment site be maintained below a concentration which is escharotic to the healthy tissue. Although the effective concentration of zinc chloride as well as nordihydroguaiaretic acid delivered to the treatment site depends, inter alia, upon the carrier and other additives included in the formulation, ordinarily the concentration of nordihydroguaiaretic acid in the formulation will range from about 0.1 to about 30 weight percent and the concentration of zinc chloride in the formulation will range from about 0.05 to about 35 weight percent. These ranges are provided by way of description and not by way of limitation since it is recognized that the concentration may be adjusted over a wide range depending on the carrier material, number of applications used, etc., as described hereinabove.

The advantages and efficacious results obtained from the instant compositions of catecholic butanes and ionic zinc allows the concentrations of the catecholic butane and zinc to be reduced to lower, more toxicologically acceptable levels while obtaining comparable or superior results to the use of higher concentrations of individual components. Thus, the concentration of zinc chloride can be reduced to below an escharotic level in the formulation in the instant compositions while still achieving efficacious results.

The pH of the formulation is important in assuring stability of the catecholic butane as well as assuring that the formulation is physiologically acceptable to the patient. Many of the catechols, particularly nordihydroguaiaretic acid, are susceptible to oxidation, for example, by air. Such oxidation can result in discoloration of the formulation rendering it unacceptable for pharmaceutical use. These catechols are more stable against oxidation at lower pH levels. Therefore, it is preferred that if the formulation is to be exposed to oxidizing conditions the pH be maintained below about 7 and preferably below about 6 in order to provide maximum stability for the catechol against oxidation. However, if oxidizing conditions can be avoided, for example, by storage of the formulation under an inert atmosphere such as nitrogen, a higher pH can be used. The pH of the formulation may be maintained through the use of toxicologically-acceptable buffers. Such buffers are well known in the pharmaceutical formulation art, and include hydrochloric acid buffer, acid phthalate buffer, phosphate buffer and citric acid/sodium citrate buffer.

It is well known that such catechols are effective antioxidant agents. It has been found that the presence of ionic zinc in a catecholic butane formulation substantially retards the rate of oxidation of the catechol, i.e. increases the stability of the catecholic butane to oxidation. This has significant advantages in that the introduction of unknown oxidation products of the catecholic butanes is minimized and the shelf-life of the pharmaceutical compositions is increased.

While not intending to be bound by a possible explanation of this not fully understood phenomena, experimental evidence set forth in the instant examples indicates that the ionic zinc serves to stabilize the semiquinone free radical and radical-anion intermediates formed during the oxidation process, possibly by forming a complex with the catechol. Surprisingly, zinc ions dramatically decreased the decay rates of these radicals compared to other metal ions tested. Consequently, the stability to oxidation of a catecholic butane formulation such as one containing nordihydroguaiaretic acid can be increased by the addition of zinc ions in the form as discussed hereinabove. The presence of ionic zinc in a molar ratio of catecholic butane to zinc of at least about 50:1 increases the stability of the catechol; however, it is referred that the molar ratio of catecholic butane to zinc be about 1:5, and most preferably about 1:2 with an excess of zinc in the range of about 2:1 to 10:1.

In topical applications the instant compositions are applied to the affected area or afflicted situs of the patient. The term "topical" refers herein to the surface of the epidermal tissue, especially the skin, the surface of tumors on the skin which have been debrided or otherwise modified, as well as sites from which solid tumors have been removed either from the skin or internally. The instant compositions are particularly useful in conjunction with surgery for removal of internal cancers to eradicate residual tumor cells and act as a prophylactic against local recurrence and metastatic spread of the tumor. The instant compositions may be applied to the effected area in lieu of surgery when there are cosmetic considerations due to the normally improved appearance of healed situs treated with the instant compositions compared to surgery alone.

Application by injection can be used for treatment of solid tumors in which removal by surgery is not desired or for which surgery is not medically advisable. In this procedure the instant composition is injected directly into the tumorous cells.

In preparing a formulation suitable for topical application, the catecholic butane is normally mixed with a suitable solvent. Examples of solvents which are effective for this purpose include ethanol, acetone, acetic acid, aqueous alkaline solutions, dimethyl sulfoxide, glycerine, glycerol, propylene glycol, nonoxynol, ethyl ether, polyethylene glycol, etc. The zinc ions, commonly in the form of a toxicologically-acceptable salt, are mixed with a suitable solvent for the zinc salt such as water or polyethylene glycol of low molecular weight, e.g. 200–400. The ionic zinc can be added in the form of readily available organic salts such as acetates or other aliphatic acid salts and/or as the preferred inorganic salt, zinc chloride. In the event there is not complete solubilization, the mixture can be milled to obtain a fine suspension.

The compositions of the instant invention have also been found to be useful in the treatment of lesions and draining wounds which show impaired healing. As used herein the term "lesion" refers to any pathological or traumatic discontinuity of tissue. A "wound" is a lesion which results from a bodily injury caused by physical means. Lesions which do not readily heal can be manifestations of conditions, diseases or infections, for example, cutaneous ulcers, osteomyletis, acne vulgaris, draining fistulas, etc. Not uncommonly, lesions do not heal properly and continue to drain which results in discomfort to the patient and a continued threat of severe infection. Such conditions in which tissue does not readily grow to heal the lesion or wound can be the result of bacterial infection or other causes not fully understood. Exposed areas created by the sloughing off of necrotic matter, generally result in pus formation (suppuration).

Direct contact of the exposed area of the wound or lesion with the instant compositions has been found in clinical studies to substantially aid the healing process, possibly by inducing the formation of granulation tissue. This promotion of healing has significant advantages, for example, in the treatment of solid tumors directly or the situs from which such tumors have been surgically removed in that healing is promoted concurrently with inhibiting the growth of any tumor cells which might remain at the site of surgery.

The catecholic butane composition and the source of ionic zinc are mixed in appropriate amounts to achieve the desired concentrations. When the formation of a metal chelate or complex is believed desirable, the order of mixing of ingredients and the pH of the formulation may be critical. When chelates or complexes are desired, compounds which can serve as counter-ligands are preferably provided so that discreet "molecular" entities are formed rather than polymers of indeterminant length. Such counter-ligands include ethylenediamine tetraacetic acid (EDTA), ethylenediamine diacetic acid (EDDA), ethylenediamine, ammonia, ethanolamine, amino acids, etc.

The following examples are included by way of illustration and not by way of limitation. Unless otherwise indicated, the nordihydroguaiaretic acid used in the instant Examples was the meso-isomer and is designated NDGA. Other isomers are indicated, e.g., d,l-NDGA.

EXAMPLE I

The catecholic butane 1-(3,4-dihydroxyphenyl)-4-(2,3,4-trihydroxyphenyl) butane was prepared by the following procedure.

500 grams of 3,4-dimethoxydihydrocinnamic acid was suspended in 1.6 liters of methanol containing 250 ml of 2,2-dimethoxypropane. To this mixture was added dropwise a solution made by adding 20 ml. of acetyl chloride to 400 ml of methanol. The resulting mixture was stirred overnight at room temperature and finally at reflux for one hour. The solvent was evaporated to give a syrup in quantitative yield, 533 g.

To 912 ml. of lithium aluminum hydride (1M in THF) was added dropwise 213 g. of 3,4-dimethoxydihydrocinnamic acid methyl ester dissolved in 900 ml of dry THF at such a rate as to maintain gentle reflux (5 hours). The reaction mixture was stirred overnight at room temperature, cooled in an ice bath and treated dropwise with ammonium chloride solution (saturated) (104 ml) over a two hour period. After stirring for several hours, the reaction mixture was diluted with 500 ml. of THF, filtered and the filtrate evaporated in a vacuum to give 160 g. (86%) of a light yellow oil.

3-(3,4-dimethoxyphenyl) propanol (202 g) was added to 218 ml of triethylamine in one and half liters of methylene chloride. This solution was cooled to $-10°$ C. in an ice salt bath and 87.6 ml. of methanesulfonyl chloride was added dropwise over a one and a half hour period while stirring rapidly. Stirring was continued for another hour and the mixture was washed with 700 ml. of ice water, 700 ml. of 3N hydrochloric acid, 700 ml. of saturated sodium bicarbonate and finally with 700 ml. of brine. The organic phase was dried with sodium sulfate and evaporated in a vacuum to give an orange oil in quantitative yield, 282 g.

3-(3,4-dimethoxyphenyl) propanol methanesulfonate, 282 g., (1.029 mol.); KBr, 282 g. (2.37 mol.) and dicyclohexano-18-crown-6, 19.2 g. (0.01515 mol.) were stirred in refluxing acetonitrile, 2.8 liters (dried over 3A molecular sieves) for 22 hours. The mixture was filtered and the filtrate evaporated in a vacuum to give an orange oil, 267 g. The product could be purified by vacuum distillation at 0.5 mm Hg, b.p.=113°–116° C.

3-(3,4-Dimethoxyphenyl) propyl bromide, 25.9 g., in 50 ml. of dry tetrahydrofuran (dried distillation from LAH) was placed in a dropping funnel. Magnesium powder, 2.5 g., and a trace of iodine was placed in a dry three neck flask with nitrogen inlet and reflux condenser. The reaction started upon addition of the liquid reactant and reflux was continued over a three hour period during which time the metal dissolved in the stirred solution. The reaction was cooled and the volume made up to 200 ml. to form a 0.5M solution in dry THF.

2,3,4-Trimethoxybenzaldehyde, 1.96 g. (0.01 mole), dissolved in 20 ml. of dry THF and 20 ml. of the 0.5M Grignard reagent from 3-(3,4-dimethoxyphenyl)propyl bromide in THF was added dropwise at ice temperature. The mixture sat over night at room temperature. The solution was evaporated in a vacuum and 20 ml. of ethanol was added carefully followed by excess sodium borohydride. Refluxing for a few minutes destroyed the yellow color of the small amounts of ketone and other unsaturated impurities formed from oxidation of the product. Most of the ethanol was evaporated and the residue partitioned between water and ether, 50 ml. of each. The ether phase was dried over sodium sulfate and evaporated to give 4.65 g. of a pale yellow oil.

The 4-(3,4-dimethoxyphenyl)-1-(2,3,4-trimethoxyphenyl) butanol, 3.65 g., was treated with excess sodium hydride, 1 g., and methyl iodide, one ml, in 25 ml. of dry dimethylformamide during one hour of stirring. Water was added carefully dropwise at first and finally 500 ml. of water was added. The product was extracted three times with 50 ml. of chloroform and the solvent evaporated to give a colorless crude oily product that can be used in the next step without further purification.

About 100 ml of anhydrous ammonia was condensed into a three necked flask with a dry ice condenser and dry ice bath. The flask was protected from moisture with a soda-lime tube and flow of dry nitrogen. One gram of clean sodium metal was dissolved in the liquid ammonia and the whole of the crude product in 20 ml of dry tetrahydrofuran was added as quickly as possible. The dark blue solution was stirred rapidly for twelve minutes before enough methanol was added to destroy the blue color. Evaporation of the solvent under a vacuum gave a thick residue to which 500 ml. of water was added. The water solution was extracted twice with 50 ml. of chloroform that left three grams of oily residue on evaporation. Chromatography of this crude product on 300 g. of silica-gel using chloroform as an eluate gave 2.3 of pure 1-(3,4-dimethoxyphenyl)-4-(2,3,4-trimethoxyphenyl) butane (one spot on TLC).

A 1.15 g. sample of 1-(3,4-dimethoxyphenyl)-4-(2,3,4-trimethoxyphenyl) butane was refluxed for nine hours in 50 ml. of 48% hydrobromic acid under an inert nitrogen atmosphere. Standing over the weekend allowed 641 mg. of tan product to settle out in the freezer. This material was recrystallized under inert atmosphere from methanol-water 1:20 to give light pink crystals, m.p.=165°-167° C.

The following compounds were prepared by a similar procedure:

(a) 1-(3,4-Dihydroxyphenyl)-4-(3,4,5-trihydroxyphenyl)butane;

(b) 1-(3,4-Dihydroxyphenyl)-4-phenylbutane (c) 1-(3,4-Dihydroxyphenyl-4-(2,5-dihydroxyphenyl) butane;

(d) 1,4-Di(3,4-dihydroxphenyl)-1,2,3,4-tetramethylbutane (e) 1,4-Di(3,4-dihydroxyphenyl)-2-methyl-3-ethylbutane (f) 1,4-Di(3,4-dihydroxyphenyl)-1-propyl-2-methyl-3-ethylbutane

EXAMPLE 2

A number of experiments were performed to determine the antitumor activity of the compositions according to the invention against B-16 melanoma and Sarcoma-180 solid tumor growth in mice.

The test compounds comprised varying compositions of nordihydroguaiaretic acid (NDGA), zinc chloride and excipients formulated into a polyethylene glycol (Pego) base to obtain an appropriate consistency for application. Some of the compositions included an additional compound, quercetin. The wt. ratio of zinc chloride to NDGA generally ranged from about 4:1 to 1.5:1.

Both types of the tumors were grown intradermally or subcutaneously in the mice. When adequate tumor size was achieved, the mice were divided into control and test groups. The tumors were punctured uniformly and then either a test compound or a control by topical application was applied to the surface of the tumor. In some cases, the tumors were injected with the test compound or the control.

Almost all of the tumors demonstrated a significant reduction in size or were completely eliminated by the test compounds containing zinc chloride and NDGA.

Exemplary compositions of the mixtures are given in Table 2:

TABLE 2

| Mixture | ZnCl$_2$ | NDGA | EDTA | H$_2$O | PEGO |
|---------|----------|------|------|--------|------|
| 53 | 27.5 | 6.9 | 14.7 | 18.3 | 32.6 |
| 54 | 28 | 6.8* | 14.7 | 18.2 | 32.9 |
| 55 | 16.4 | 6.9 | 8.6 | 18.0 | 32.2 |

*d,l NDGA

These mixtures were tested for their potential antitumor activities against B-16 melamonas grown in mice in accordance with the procedure discussed above. The results are given in table 2a.

TABLE 2a

| Mixture | n | T/C | Tumor Size (Control) | % Clear (Control) | % Survival (Control) |
|---------|---|-----|----------------------|-------------------|----------------------|
| 53 | 10 | 0 | 0 | 80 | 80 |
|    |    |   | (575 ± 270) | (0) | (60) |
| 53 | 10 | 8 | 51 ± 118 | 70 | 100 |
|    |    |   | (711 ± 286) | (0) | (100) |
| 54 | 10 | 0 | 0 | 60 | 100 |
|    |    |   | (711 ± 286) | (0) | (100) |
| 55 | 10 | 73 | 522 ± 356 | 10 | 100 |
|    |    |   | (711 ± 286) | (0) | (100) |

EXAMPLE 3

Fifteen older dogs having perianal adenomas were treated topically with the NDGA plus zinc salt ointment having a strength of 55% (w/w).

To 36.7 grams of powdered Larrea divaricata extract, containing 85% of weight NDGA, were added 24.5 grams of powdered rosehips and the mixture was mixed in a blender for 5 minutes. The blended mixture was then mixed with 100 milliliters of an aqueous solution containing 185.9 grams zinc chloride to form a paste. The paste was allowed to stand at room temperature for 24 hours. Thereafter, it was stirred and then placed in a screw-capped glass container. The container was placed in a humidified oven at 40° C. for 5 days. This incubated paste was then suspended in 500 milliliters of water and shaken at room temperature for 24 hours on a reciprocating shaker. The zinc chloride extract solution was then evaporated to near dryness on a rotary evaporator at 90° C. under reduced pressure. A sufficient quantity of this dried zinc chloride extract was added to 120 grams of an ointment base consisting of 10% (w/w) stearyl alcohol and 90% (w/w) polyethylene glycol to obtain an ointment containing 70% (w/w) of the extract.

The normal treatment for such a condition is surgery; however, these older dogs were poor surgical risks. The tumor of each dog was biopsied and the ointment was applied topically into the biopsied incision. The duration of treatment varied depending upon the severity of the adenoma. Dogs with simple circumscribed adenomas required only one treatment. The dogs with more advanced adenomas generally required more than one treatment which were given three to five days apart. The treatment was successful in thirteen of the fifteen dogs. The treatment was not successful in two of the dogs which had extremely advanced cases of perianal adenomas.

EXAMPLE 4

Test compositions were prepared according to the following general method to test the activity of the compositions according to the invention against human breast adenocarcinoma, MX-1.

The NDGA, BHT (butylated hydroxytoluene), and Pego 400 were measured and mixed together with heating until melted and dissolved. Pego Base (50% Pego 400, 45% Pego 3350 and 5% stearyl alcohol) was prepared by mixing and heating the components together in a separate container until they dissolved. $ZnCl_2$ and EDTA were dissolved in water with heating and stirring in a separate container. The ingredients in each of the separate containers were added together in amounts needed to give the concentrations desired and allowed to cool with vigorous mixing. Any further dilution to achieve desired wt/wt % was achieved by adding Pego 400. When an ingredient was omitted from a particular composition, the amount of the missing ingredient was supplied by adding additional Pego 400. Wt/wt % of compositions utilized in this experiment are given below.

| Ingredient in wt/wt % | Test Composition | | |
|---|---|---|---|
| | 1 | 2 | 3 |
| $ZnCl_2$ | 4.3 | 4.3 | 4.3 |
| Purified water | 2.6 | 2.6 | 2.6 |
| EDTA | — | 2.1 | 2.1 |
| NDGA | 0.66 | 0.66 | 0.66 |
| BHT | 0 | 0.66 | 0 |
| Pego 400 | 91.04 | 88.28 | 88.94 |
| Pego Base | 1.4 | 1.4 | 1.4 |

The test compositions were tested in five athymic mice implanted with human breast adenocarcinoma, MX-1. Results are given in Table 4 and confirm the activity of these combinations of the phenolic butane, NDGA, and zinc ions.

TABLE 4

| Test Composition | Tumor Free at 60 days | Premature Death | Tumor at Death | Tumor Recurrence |
|---|---|---|---|---|
| 1 | 4 | 1 | 0 | 0 |
| 2 | 4 | 0 | 1 | 1 |
| 3 | 5 | 0 | 0 | 0 |

EXAMPLE 5

In order to demonstrate the activity and use of zinc ions from other salts, two test compositions were prepared according to the procedure previously described. In these, the zinc chloride was replaced by zinc iodide and zinc bromide. Concentrations of the ingredients are given below in wt/wt percent.

| Ingredient | Test Composition | |
|---|---|---|
| | 1 | 2 |
| BHT | 0.65 | 0.7 |
| EDTA | 2.1 | 2.3 |
| NDGA | 0.98 | 1.1 |
| $ZnI_2$ | 3.9 | — |
| $ZnBr_2$ | — | 4.3 |
| $H_2O$ | 2.6 | 2.9 |
| Pego Base | 1.4 | 0 |

| Ingredient | Test Composition | |
|---|---|---|
| | 1 | 2 |
| Pego 400 | 88.37 | 88.68 |

The two compositions were tested for antitumor activity against human breast adenocarcinoma, MX-1, grown in five athymic mice as previously described. The results are given in Table 5.

TABLE 5

| Test Composition | Tumor Free at 60 days | Premature Death | Tumor at Death | Tumor Recurrence |
|---|---|---|---|---|
| 1 | 4 | 1 | 0 | 0 |
| 2 | 4 | 0 | 1 | 0 |

EXAMPLE 6

A test composition of NDGA plus zinc chloride was investigated for and found to possess antineoplastic activity against xenografts of the following human cancers: lung squamous cell carcinoma, LX-1; breast adenocarcinoma, MX-1; renal cell cancer, RX-1; brain cancer (glioma); melanoma; and colon cancer, CX-1. The test composition with the approximate wt/wt percentages given below was prepared according to the procedure previously described in Example 4. The control composition was Pego 400.

| Ingredient | Test Composition 1 | Control |
|---|---|---|
| BHT | 0.16 | — |
| EDTA | 2.10 | — |
| NDGA | 0.66 | — |
| $ZnCl_2$ | 4.26 | — |
| $H_2O$ | 2.62 | — |
| Pego Base | 1.43 | — |
| Pego 400 | 88.77 | 100 |

The composition was then tested for its effect on human tumors of varying origin implanted in athymic mice as previously described. Generally, there were ten mice in each group tested with Pego 400 control. Instances in which the number of mice varied are specifically indicated.

Results are given in Table 6.

TABLE 6

| Tumor Type | Test Composition | Tumor Free at 60 Days | Premature Death | Tumor At Death | Recurrence |
|---|---|---|---|---|---|
| LX-1 (lung) | 1 | 8 | 0 | 2 | 0 |
| | control | 0 | 0 | 5 | 0 |
| MX-1 (breast) | 1 | 8 | 0 | 2 | 1 |
| | control | 0 | 0 | 2 | 0 |
| RX-1 (Renal) | 1 | 8 | 1 | 1 | 0 |
| | control | 0 | 1 | 5 | 0 |
| Glioma (Brain) | 1 | 6 | 0 | 0 | 0 |
| | control | 0 | 0 | 2 | 0 |
| Melanoma | 1 | 10 | 0 | 0 | 0 |
| | control | 0 | 0 | 5 | 0 |
| CX-1 (Colon) | 1 | 8 | 1 | 2 | 0 |
| | control | 0 | 0 | 5 | 0 |

EXAMPLE 7

A number of catecholic butane compositions were formulated into test compositions according to the following general method, and tested for activity against human breast adenocarcinoma, MX-1.

Zinc chloride was dissolved in Pego 400 to prepare a stock solution. The amount of organic compound required to give the final concentration given below was separately dissolved in Pego 400.

The two solutions were mixed to give a final concentration in each test composition of zinc chloride at 0.69 wt/wt % and each organic compound at a molar concentration equivalent to 4.4 wt/wt % of NDGA.

The test compositions in Table 7 were tested for their effectiveness as antitumor agents against xenografts of the human breast adenocarcinoma, MX-1, grown in athymic mice. They were administered to five animals by intratumor injection. Animals were administered 0.05 ml of test composition unless indicated otherwise.

TABLE 7

| Animal Organic Compounds | Tumor Free 60 Days | Premature Death | Tumor at Death | Tumor Recurrence |
|---|---|---|---|---|
| Pego control | 0 | 0 | 5 | 0 |
| NDGA | 4 | 1 | 0 | 0 |
| d,l NDGA | 5 | 0 | 0 | 0 |
| NDGA Tetracetate | 4 | 0 | 1 | 0 |
| NDGA Tetrapropionate | 4 | 0 | 1 | 1 |
| 1,4-bis(3'-methoxy-4'-hydroxyphenyl Butane | 2 | 0 | 3 | 0 |
| 1,4-bis(3'-methoxy-4'-hydroxyphenyl)-2,3-dimethyl butane | 4 | 0 | 1 | 0 |
| 1-(3',4'-dihydroxyphenyl)-4-(2',3',4'-trihydroxyphenyl)-butane | 2 | 1 | 3 | 0 |
| 1-(3',4'-dihydroxyphenyl)-4(3',4',5'-trihydroxyphenyl)-butane | 3 | 0 | 2 | 1 |
| 1-(3',4',-dihydroxyphenyl)-4-(2',5'-dihydroxyphenyl)-butane | 5 | 0 | 0 | 0 |
| 1-(3',4'-dihydroxyphenyl)-4-phenyl butane | 3 | 1 | 1 | 0 |
| 1-(3',4'-dihydroxphenyl)-4-(2',4'-dihydroxyphenyl)-butane | 2 | 0 | 3 | 3 |

EXAMPLE 8

Various zinc salts were tested in combination with NDGA to determine the effectiveness of the compositions according to the invention against xenografts of human breast adenocarcinoma, MX-1, grown in groups of five athymic mice.

The tumors were implanted subcutaneously in the left flank of the mice and the tumors were allowed to grow until they reached an approximate size of between 25 and 100 mm² (length×width). The mice were given a single 0.010 ml intratumor injection of the test composition. The concentration of the various metal salts in the test compositions was 0.73% (wt/wt) metal salt and 1.0% (wt/wt) NDGA, in a PEGO 400 base. The results of these test compositions are summarized in Table 8.

TABLE 8

| Test Compound | Tumor Free at 60 Days | Premature Death | Tumor at Death | Tumor Recurrence |
|---|---|---|---|---|
| ZnCl$_2$ | 4 | 0 | 3 | 3 |
| ZnSO$_4$.7H$_2$O | 2 | 0 | 3 | 3 |
| ZnBr$_2$ | 2 | 0 | 3 | 3 |
| Zn Acetate.2H$_2$O | 2 | 0 | 3 | 3 |
| Zn(NO$_3$)$_2$.6H$_2$O | 3 | 1 | 1 | 1 |
| ZnCl$_2$ (without NDGA) | 1 | 0 | 19 | 19 |

In a separate trial, solubilized zinc gluconate demonstrated efficacious results in the in vitro inhibition of clonogenic human lung tumor cells (LX-T) when combined with NDGA.

EXAMPLE 9

This example describes the antineoplastic activity of compositions containing NDGA and zinc ions in clinical studies on human patients with basal cell epithelioma.

Compositions as set forth in Table 9 suitable for topical application were prepared:

TABLE 9

| Composition Compounds | A | B | C | D | E |
|---|---|---|---|---|---|
| zinc chloride | 29.8 | 1.0 | 5.0 | 10.0 | 20.0 |
| NDGA | 4.6 | 4.6 | 4.6 | 4.6 | 4.6 |
| EDTA | 14.7 | 0.49 | 2.47 | 4.93 | 0 |
| BHT | 1.1 | 1.1 | 1.1 | 1.1 | 0 |
| stearyl alcohol | 0.5 | 0.5 | 0.5 | 0.5 | 0.5 |
| H$_2$O | 18.3 | 18.3 | 18.3 | 18.3 | 18.3 |
| Pego 400 | 26.4 | 26.4 | 26.4 | 26.3 | 26.4 |
| Pego 3350 | 4.5 | 4.5 | 4.5 | 4.5 | 4.5 |

The water was heated to about 80°–90° C. with stirring, and zinc chloride was added. The EDTA was next added with mixing until dissolved. In a separate container the polyethylene glycol 400 was heated to about 80°–90° C. with stirring, the NDGA was added thereto, then the BHT, and this mixture was added to the zinc chloride-EDTA solution with stirring. The entire mixture was then cooled to about room temperature and passed through a number 3 roller mill until smooth. The polyethylene glycol 3350 was then heated to about 80°–90° C. and the milled ingredients added thereto with mixing.

The surface of the lesions were tape stripped prior to each application. The test medication was applied directly to the lesion with a coating approximately 2 mm thick, and covered with a dressing. After a minimum of seven (7) days, a second application was applied at the discretion of the investigator. The dose ranged from 20–350 mg/cm² with as much as 500 mg/cm² utilized for deep tumors. To determine the effect of the test compound on the malignant neoplasma, an excisional biopsy was obtained 30 days after the initial treatment.

Of the fifty seven patients with basal cell epithelioma who were treated with compositions A, B, C or D, twenty showed negative biopsies, i.e., no evidence of tumor, at the conclusion of the treatment period.

EXAMPLE 10

Fifty-nine (59) human patients with actinic keratosis were treated with NDGA plus zinc containing compositions B, C, or D as in Example 9. The test medication was applied directly to the lesion with a coating of approximatley 2 mm and confined to the lesion margin. A dressing was applied to the lesion. A visual examination and measurement of the lesion was performed 7 and 14 days following the initial treatment. At the discretion of the investigator, a second treatment with the same test compound was applied. In order to determine whether the test compound eradicated the premalignant neoplasm, a punch biopsy was obtained 30–60 days after the initial treatment. If the biopsy report was negative, i.e., no tumor, the patient was examined every 6 months for a period of 12 months. If the biopsy continued to show evidence of actinic keratosis, the patient was withdrawn from the study and treated with conventional therapy.

The fifty nine (59) patients had a total of 61 lesions. After treatment with the NDGA plus zinc salt compositions, thirty two of the lesions showed negative biopsies, i.e., there was no evidence of actinic keratosis.

EXAMPLE 11

Canine patients with various tumor lesions were treated with compositions A, C, D or E of Example 9. The animals were restrained from movement for two hours physically or with sedatives (e.g. 0.03 mg oxymorphone/lb.sq with atropine sulfate). After clipping, washing and measuring the tumor size, the skin surface was abraded until bleeding occurred. To enhance the penetration of the test compositions for large or subdermal tumors, a 20 or 22 gauge needle was used to puncture the tumor. After blotting the skin dry of blood, the tumor site was covered with a 1–2 mm coating of the test composition extending 5 mm peripherially. After 2 hours, the compound was wiped off and the area gently cleansed. The test composition was applied up to three times within a two-week interval or until the tumor cleared. The results of the canine studies are given in Table 11, and show that in canine patients, seven of the twenty four animals showed complete remissions, and another four showed partial remission.

TABLE 11

| | Test Composition | No. Animal Tested | Cure | Partial Effect | No Effect |
|---|---|---|---|---|---|
| Mast cell tumors | A | 3 | 1 | 1 | 1 |
| Mast cell tumors | C,D | 6 | — | 2 | 4 |
| Mast Cell tumors | E | 2 | 1 | — | 1 |
| Squamous cell carcinoma | A | 1 | 1 | — | — |
| Mammary Adenoma | A | 2 | 1 | — | 1 |
| Perianal Adenoma | A | 7 | 1 | 1 | 5 |
| Perianal Adenitis | A | 1 | — | — | 1 |
| Perianal Cyst (Benign) | A | 1 | 1 | — | — |
| Basal Cell Carcinoma | A | 1 | 1 | — | — |
| Totals | | 24 | 7 | 4 | 13 |

EXAMPLE 12

Equine patients with various tumor lesions were treated with compositions A, C, D, or E of Example 9. Melanoma, sarcoid and squamous cell carcinoma lesions were removed to skin level by surgical debulking; for papillomas, the lesion tips were removed. After hemostasis, the tumor site was covered liberally with the test compound extending 5 mm peripherially. Two weeks later, the crust was removed, the lesion area abraded and the test compound applied topically. After an additional two weeks, any crust was again removed from the lesion and the area abraded. The same test compound was again applied topically Four weeks later, a biopsy of the lesion area was performed. The results of the equine studies in Table 12, show that NDGA plus zinc salt compositions show good activity against the tumor lesions in equine patients. The high activity of the composition against Papillomas, known to have viral components, indicated the activity of these compositions.

TABLE 12

| Lesion | Test Composition | No. Animals Tested | Cure | Partial | No Effect |
|---|---|---|---|---|---|
| Papillomas | A | 4 | 4 | — | — |
| Melanoma | A | 4 | 3 | — | 1 |
| Squamous Cell Car. | A | 3 | 2 | 1 | — |
| Sarcoid | A | 5 | 4 | 1 | — |
| Sarcoid | C or D | 6 | 1 | 2 | 3 |
| Sarcoid | E | 5 | 5 | — | — |
| | | 27 | 19 | 4 | 4 |

EXAMPLE 13

The in vivo antitumor effect of the interaction of NDGA and $ZnCl_2$ at various ratios was determined against MX-1 (human breast adenocarcinoma) cells.

Male or female athymic Balb/c mice, six to eight weeks of age and weighing 20 to 35 grams were used. MX-1 cells were cultured in the standard RPMI-1640 media and implanted subcutaneously in the flank of the nude mice in order to propagate the tumor line. Nude mice were implanted with 25 mg of the MX-1 solid tumor fragments. Tumors which reached the 25–100 mm² range were used for the experiment. 0.1 ml of the test compound was injected directly into the tumor. The tumors were measured periodically to determine their weight calculated by using half the product of the length times the width times the height of the tumor. The procedure was repeated at regular intervals until 60 days after the initial treatment or all mice had died. Mice which showed no evidence of tumors were kept for 60 days to evaluate the potential for tumor recurrence, at which time tumor characteristics, if any, were recorded. Table 13 contains the results of the experiments using mixtures of NDGA and $ZnCl_2$ as well as the results of experiments with NDGA alone or with $ZnCl_2$ alone.

The effective doses (ED$_x$) at different response levels (x), determined in micromoles for ZnCl$_2$ alone, NDGA alone, and for the combination of ZnCl$_2$ in different molar ratios with NDGA are provided in Table 13.

The significant reduction in amount of either NDGA or zinc chloride required when given in combination is evident from the data. It is also seen that the total amount required for ED$_x$ doses of the composition made up of NDGA plus zinc chloride is significantly less than the ED$_x$ dose of NDGA or zinc chloride alone.

TABLE 13

| | MICROMOLES | | | |
|---|---|---|---|---|
| | ED$_{50}$ | ED$_{75}$ | ED$_{90}$ | ED$_{95}$ |
| NDGA | 13.6 | 25.7 | 48.3 | 74.3 |
| ZnCl$_2$ | 15.7 | 22.2 | 31.6 | 40.1 |
| NDGA (1:1)[1] + ZnCl$_2$ | 5.7 | 8.8 | 13.6 | 18.2 |
| (1:2)[2] | 4.6 | 6.2 | 8.4 | 10.4 |
| (1:2)[3] | 2.3 | 3.1 | 4.2 | 5.2 |

[1] Calc'd as micromoles NDGA or ZnCl$_2$.
[2] Calc'd as micromoles ZnCl$_2$
[3] Calc'd as micromoles NDGA

EXAMPLE 14

Experiments were carried out indicating that zinc acts to stabilize the radical intermediate formed during oxidation of NDGA, thereby effectively stabilizing the NDGA and allowing it to exert its effect over a longer period of time before it is oxidatively inactivated.

Aqueous ethanolic solutions of NDGA with and without various metal salts at pH 4, 7, and 10 were analyzed in an ESR spectrometer for the presence of free radical ion.

The maximum peak height to minimum peak height of the ESR signal was measure over time. The reduction in ESR with time was used as a measure of free radical decay. The slope of free radical decay normalized to that of 3-hydroxytyrosine (DOPA) provided a measure of the relative rate constant of semiquinone free radical decay from NDGA.

The various rate constants, K$_d$, are given in Table 14. These results show that there is a substantial decrease in the rate of decay of the NDGA semiquinone radical/radical anion intermediate when zinc is present as opposed to magnesium, iron or cobalt.

TABLE 14

| | Rate Constants K$_d$ | |
|---|---|---|
| Solution Composition | pH | K$_d$(M$^{-1}$ sec$^{-1}$) |
| NDGA | 4 | 1.05 × 10$^4$ |
| | 7 | 1.05 × 10$^4$ |
| | 10 | 4.0 × 10$^3$ |
| NDGA + ZnCl$_2$ | 4 | 5.1 × 10$^2$ |
| | 7 | 4.2 × 10$^3$ |
| | 10 | 1.7 × 10$^2$ |
| NDGA + MgCl$_2$ | 4 | 1.0 × 10$^4$ |
| | 7 | 1.3 × 10$^4$ |
| | 10 | 2.9 × 10$^3$ |
| NDGA + FeCl$_2$ | 7 | undetectable signal |
| NDGA + CoCl$_2$ | 7 | undetectable signal |
| DOPA | 7 | undetectable signal |
| DCPA + ZnCl$_2$ | 7 | 1–2 × 10$^4$ |

While there have been described what are presently believed to be preferred embodiments of the invention, it will be apparent to a person skilled in the art that numerous changes can be made in the ingredients, conditions and proportions set forth in the foregoing embodiments without deaprting from the invention as described herein and as defined in the appended claims.

What is claimed is:

1. A pharmaceutical composition comprising at least 1 catecholic butane of the formula:

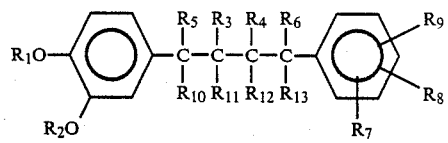

wherein R$_1$ and R$_2$ are independently H, lower alkyl, or lower acyl;

R$_3$, R$_4$, R$_5$, R$_6$, R$_{10}$, R$_{11}$, R$_{12}$ and R$_{13}$ are independently H or lower alkyl;

R$_7$, R$_8$ and R$_9$ are independently H, hydroxy, lower alkoxy or lower acyloxy; and ionic zinc.

2. The compositions according to claim 1 wherein said ionic zinc is in the form of a zinc salt or chelate of said catecholic butane.

3. The compositions according to claim 1 wherein said ionic zinc is in the form of a zinc salt or a chelate of zinc.

4. The compositions according to claim 1 wherein the molar ratio of said catecholic butane to said ionic zinc is between about 10:1 and 1:20.

5. The composition according to claim 4 wherein the catecholic butane is nordihydroguaiaretic acid.

6. The composition according to claim 5 wherein the source of the ionic zinc is zinc chloride.

7. Pharmaceutical composition comprising a pharmaceutically acceptable carrier and the composition of claim 6 wherein said ionic zinc is derived from a pharmaceutically acceptable salt.

8. A pharmaceutical composition comprising a pharmaceutically acceptable carrier and the composition of claim 4 wherein said ionic zinc is derived from a pharmaceutically acceptable salt.

9. A pharmaceutical composition comprising a pharmaceutically acceptable carrier and the composition of claim 5 wherein said ionic zinc is derived from a pharmaceutically acceptable salt.

10. The composition according to claim 1 wherein said catecholic butane contains at least one lower alkyl ether derivative moiety.

11. The composition according to claim 1 wherein said catechol butane contains at least one lower acyl ether derivative moiety.

12. The composition according to claim 1, wherein the ionic zinc is a cation of a pharmaceutically acceptable soluble salt.

13. The composition according to claim 1, wherein lower alkyl is C$_1$–C$_6$ alkyl, R$_3$ and R$_4$ are C$_1$–C$_3$ alkyl and the lower acyl is a [C$_1$–C$_6$] acyl.

14. The composition according to claim 1, wherein the catecholic butane is selected from the group consisting of 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4- divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; and 1-(3,4-dihydroxyphenyl)-4-phenylbutane; 1-(3,4-dihydroxyphenyl)-4-(2,5-dihydroxyphenyl) butane.

15. The pharmaceutical composition according to claim 1 wherein the catecholic butane is nordihydroguaiaretic acid in any of its racemic forms.

16. The composition according to claim 1 wherein the catecholic butane is selected from the group consisting of nordihydroguaiaretic acid tetrapivalate, nordihydroguaiaretic acid tetrapropionate and all optical configurations thereof.

17. A pharmaceutical composition comprising a pharmaceutically acceptable carrier and the composition of claim 1.

18. A method for treating disorders of the skin, which comprises topically administering to a mammal in need of said treatment an effective amount of a composition comprising ionic zinc and at least one catecholic butane of the formula:

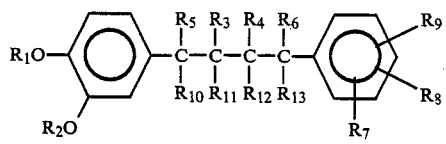

wherein $R_1$ and $R_2$ are independently H, lower alkyl or lower acyl;

$R_3$, $R_4$, $R_5$, $R_6$, $R_{10}$, $R_{11}$, $R_{12}$ and $R_{13}$ are independently H or lower alkyl;

$R_7$, $R_8$ and $R_9$ are independently H, hydroxy, lower alkoxy or lower acyloxy; and ionic zinc.

19. The method according to claim 18, wherein the catecholic butane is nordihydroguaiaretic acid, and the ionic zinc is a cation of a pharmaceutically acceptable water soluble salt.

20. The method according to claim 18 wherein the catecholic butane is selected from the group consisting of nordihydroguaiaretic acid in any of its racemic forms, nordihydroguaiaretic acid tetrapivalate, nordihydroguaiaretic acid tetrapropionate and all optical configurations thereof.

21. The method according to claim 18 wherein the disorder of the skin is actinic keratosis.

22. The method according to claim 18 wherein the disorder of the skin is a tumor.

23. The method according to claim 22, wherein 2–20 mg of composition are applied to each $cm^2$ of solid tumor.

24. The method according to claim 18 wherein the disorder of the skin is psoriasis.

25. The method according to claim 18 wherein the disorder of the skin is selected from the group consisting of tumors, actinic keratosis, acne, psoriasis, skin wounds warts, bacterial infections, fungal infections and viral infections.

* * * * *